(12) United States Patent
Heikali et al.

(10) Patent No.: US 10,857,028 B2
(45) Date of Patent: Dec. 8, 2020

(54) METHOD AND DEVICE FOR TREATING AND MANAGING DISEASED OCULAR TISSUE

(71) Applicants: Sara Heikali, Los Angeles, CA (US); Moossa Heikali, Los Angeles, CA (US)

(72) Inventors: Sara Heikali, Los Angeles, CA (US); Moossa Heikali, Los Angeles, CA (US)

( * ) Notice: Subject to any disclaimer, the term of this patent is extended or adjusted under 35 U.S.C. 154(b) by 0 days.

(21) Appl. No.: 16/119,967

(22) Filed: Aug. 31, 2018

(65) Prior Publication Data

US 2018/0369018 A1 Dec. 27, 2018

Related U.S. Application Data

(63) Continuation of application No. 15/722,569, filed on Oct. 2, 2017, now abandoned.
(Continued)

(51) Int. Cl.
*A61F 9/007* (2006.01)
*A61K 9/00* (2006.01)
(Continued)

(52) U.S. Cl.
CPC .......... *A61F 9/007* (2013.01); *A61F 9/00736* (2013.01); *A61K 9/0021* (2013.01);
(Continued)

(58) Field of Classification Search
CPC . A61K 9/0021; A61K 9/0051; A61L 2430/16; A61F 9/007; A61F 9/00736
See application file for complete search history.

(56) References Cited

U.S. PATENT DOCUMENTS

| 4,268,131 A | 5/1981 | Miyata et al. |
| 4,983,181 A | 1/1991 | Civerchia et al. |

(Continued)

FOREIGN PATENT DOCUMENTS

| CA | 2738957 A1 | 4/2010 |
| CN | 101502458 A | 8/2009 |

(Continued)

OTHER PUBLICATIONS

Ramamurthi et al., Pathogenesis, clinical features and management of recurrent corneal erosions, Eye (2006) 20, 635-644.
(Continued)

*Primary Examiner* — William H Matthews
(74) *Attorney, Agent, or Firm* — Brentwood IP Law, P.C.; Shahrooz Isaac Zaghi

(57) ABSTRACT

A method of treating and managing diseased ocular tissue in the bulbar conjunctiva comprises providing a device comprising a plurality of microneedles arranged on a substrate contacting the device with a diseased ocular tissue region formed in the bulbar conjunctiva stroma to form a plurality of micro-injury sites therein. A device comprises a contact lens substrate comprising a substantially elliptical corneal portion and a limbus portion located radially about the corneal portion. A scleral portion is located radially about the substrate. The device is at least partially degradable and/or comprises a therapeutic compound. At least a portion of the scleral portion is configured to overlay, and deliver the therapeutic compound to a diseased ocular tissue located adjacent to the cornea of a patient.

24 Claims, 7 Drawing Sheets

Related U.S. Application Data

(60) Provisional application No. 62/496,501, filed on Oct. 18, 2016, provisional application No. 62/495,976, filed on Sep. 30, 2016.

(51) Int. Cl.
*A61K 9/08* (2006.01)
*A61F 9/00* (2006.01)

(52) U.S. Cl.
CPC .......... *A61K 9/0051* (2013.01); *A61F 9/0017* (2013.01); *A61F 9/00781* (2013.01); *A61F 2210/0004* (2013.01); *A61F 2220/0016* (2013.01); *A61F 2250/0031* (2013.01); *A61K 9/0048* (2013.01); *A61K 9/08* (2013.01); *A61L 2430/16* (2013.01)

(56) References Cited

U.S. PATENT DOCUMENTS

| | | | |
|---|---|---|---|
| 5,185,152 | A | 2/1993 | Peyman |
| 5,213,720 | A | 5/1993 | Civerchia |
| 5,522,888 | A | 6/1996 | Civerchia |
| 5,716,633 | A | 2/1998 | Civerchia |
| 6,334,856 | B1 | 1/2002 | Allen et al. |
| 6,649,072 | B2 | 11/2003 | Brandt et al. |
| 7,918,814 | B2 | 4/2011 | Prausnitz et al. |
| 7,985,208 | B2 | 7/2011 | Christensen |
| 8,591,481 | B2 | 11/2013 | Britton et al. |
| 8,808,225 | B2 | 8/2014 | Prausnitz et al. |
| 9,636,253 | B1 | 5/2017 | Andino et al. |
| 2002/0138049 | A1 | 9/2002 | Allen et al. |
| 2004/0106904 | A1 | 7/2004 | Gonelli et al. |
| 2006/0251696 | A1 | 11/2006 | Winterton et al. |
| 2006/0271025 | A1 | 11/2006 | Jones et al. |
| 2007/0260201 | A1 | 11/2007 | Prausnitz et al. |
| 2008/0269666 | A1* | 10/2008 | Wang ................. A61B 17/205 604/21 |
| 2010/0010452 | A1 | 1/2010 | Paques et al. |
| 2010/0069857 | A1* | 3/2010 | Christensen ........ B29C 35/0894 604/300 |
| 2010/0228203 | A1 | 9/2010 | Quan |
| 2010/0256597 | A1 | 10/2010 | Prausnitz et al. |
| 2011/0129516 | A1 | 6/2011 | Jacob |
| 2012/0265149 | A1 | 10/2012 | Lerner et al. |
| 2015/0038905 | A1 | 2/2015 | Andino et al. |
| 2015/0209180 | A1 | 7/2015 | Prausnitz et al. |
| 2015/0277147 | A1 | 10/2015 | Kim |
| 2015/0277148 | A1 | 10/2015 | Wright et al. |

FOREIGN PATENT DOCUMENTS

| | | |
|---|---|---|
| CN | 106413798 A | 2/2017 |
| DE | 102005002465 A1 | 7/2006 |
| KR | 101746747 B1 | 6/2017 |
| WO | 2000074763 A2 | 12/2000 |
| WO | 014141079 | 9/2014 |

OTHER PUBLICATIONS

Thakrar et al., "Treatment of Recurrent Corneal Erosions", EyeNet MagazineMarch 2013, pp. 39-41.
Singh et al.,"Microneedling: Advances and widening horizons," Indian Dermatol Online J. Jul.-Aug. 2016; 7(4): 244-254.
Satish Doddaballapur, "Microneedling with Dermaroller," J Cutan Aesthet Surg. Jul.-Dec. 2009; 2(2): 110-111.
Liebl et al., "Skin Cell Proliferation Stimulated by Microneedles", Journal of the American College of Clinical Wound Specialists (2013) 4, pp. 2-6.
Cordeiro et al., "Modulating conjunctiva! wound healing," Eye (Lond). Jun. 2000;14 ( Pt 3B):536-547.
Sun et al., "Overexpression of Matrix Metalloproteinase-1 (MMP-1) and MMP-3 in Superior Limbic Keratoconjunctivitis," Invest Ophthalmol Vis Sci. Jun. 1, 2011 ;52(6):3701-3705.
MT Coroneo, "Pterygium as an early indicator of ultraviolet insolation: a hypothesis," Br J Ophthalmol. Nov. 1993; 77 (11 ): 734-739.
Mimura et al., "Pinguecula and contact lenses," J Cutan Aesthet Surg. Jul.-Dec. 2009; 2(2): 1686-1691.

* cited by examiner

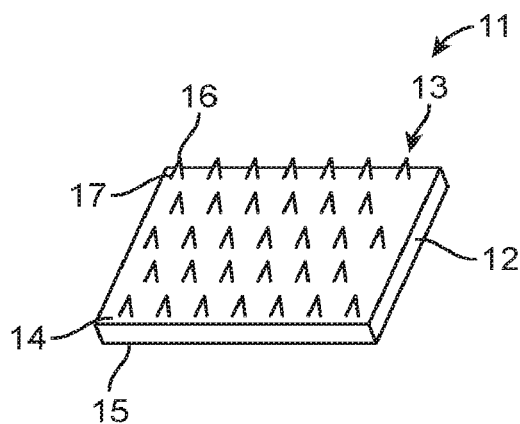
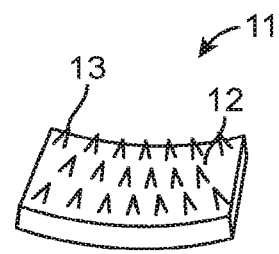
FIG. 1A
FIG. 1B
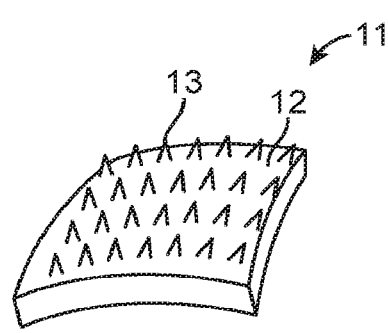
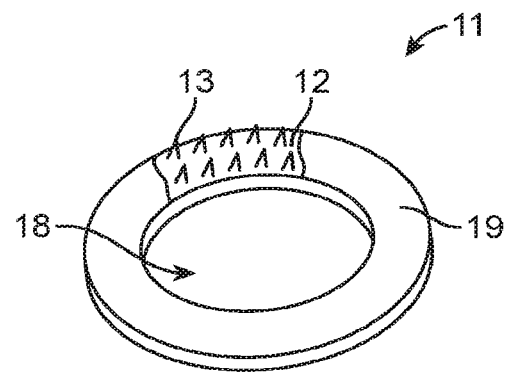
FIG. 1C
FIG. 1D
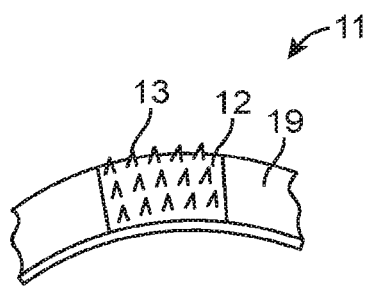
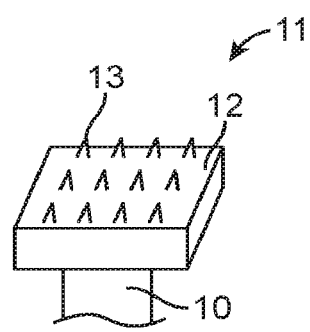
FIG. 1E
FIG. 1F

METHOD AND DEVICE FOR TREATING AND MANAGING DISEASED OCULAR TISSUE

TECHNICAL FIELD

The exemplary embodiments generally relate to methods and devices for treating ocular diseases and particularly to treating and managing diseased ocular tissue.

BACKGROUND

Various portions of the eye comprise a fibrous layer which is susceptible to disease and degradation. In some instances such diseases may be attributable to ultraviolet light exposure, which can cause collagen degeneration for example within the conjunctival stroma, as well as thinning of conjunctival epithelium. Dry or dusty environments may be other significant contributing factors. Examples of such diseases include Pinguecula and Pterygium, among others. Pinguecula, in particular, is a conjunctival degeneration of the eye tissue which consists of a benign slow growing yellow-white, opaque deposit/mass which is flat or slightly elevated and occurring in the interpalperal fissure adjacent to the limbus, usually nasal. Pingueculae are occasionally pigmented or calcified and the conjunctival lesion is usually caused by exposure to the sun/ultraviolet light and/or dry, dusty environments. Moreover, it is currently believed that a pinguecula may involve elastotic degeneration (degeneration of elastic tissue) within the conjunctival stroma, in addition to collagen degeneration.

Patients with a pinguecula(e) sometimes may experience symptoms of irritation, burning sensation, redness, and chronic dryness as the raised conjunctival lesion does not allow the natural tear film to spread evenly across the surface of the eye. For these patients, dry eye disease may be a contributing factor to pinguecula(e) growth. In mild cases, pinguecula generally requires no treatment. However to protect the eyes from sun, dust, and wind, an eyecare professional may recommend sunglasses. Further, to reduce ocular irritation, lubrication with artificial tears may be prescribed by an eyecare professional. In moderate or severe cases of an inflamed pinguecula (i.e. pingueculitis), a topical anti-inflammatory agent may be prescribed such as mild topical steroid (ex. flourometholone 0.1% four times a day) or non-steroidal anti-inflammatory drop (ex. ketorolac 0.4% four time a day). For patients with cosmesis concern of the pinguecula(e), an ophthalmologist may perform surgical excision of the pinguecula(e). In addition, if the patient is experiencing excessive irritation which is not relieved after attempting treatment options above, an eyecare professional may recommend surgical removal of the pinguecula.

A pinguecula interfering with contact lens wear may be another reason for recommended surgical removal of the lesion. Specifically, the tissue growth can result in contact lens intolerance due to the elevation of the contact lens peripheral edge overlying the pinguecula. Constant mechanical irritation of the pinguecula by the edge of the contact lens may also induce pingueculitis. To date, treatment and management of diseases such as pinguecula have been limited. In addition to the limited treatment options outlined above, there are no commercially available contact lenses, similar to those provided in this disclosure, which avoid a nasal and/or temporal peripheral bulbar conjunctival edge and/or overly a pinguecula.

SUMMARY

In an exemplary embodiment, a method of treating and managing a diseased ocular tissue in the bulbar conjunctiva comprises providing a device comprising a plurality of microneedles arranged on a substrate and contacting the device with a diseased ocular tissue region formed in the bulbar conjunctival stroma to form a plurality of micro-injury sites within the diseased bulbar conjunctival stroma. This causes release of growth factors and formation of new collagen fibrils.

In another exemplary embodiment, a device for treating and managing diseased ocular tissue in the bulbar conjunctiva, comprises a substrate and a plurality of microneedles positioned on a substrate. The microneedles are arranged and dimensioned such that when the device is brought into contact with the diseased tissue, the microneedles penetrate a diseased ocular tissue region formed in the bulbar conjunctival stroma, to produce a plurality of micro-injury sites within the diseased bulbar conjunctival stroma region. Again, this can cause release of growth factors and formation of new collagen fibrils.

In another exemplary embodiment, a device for treating and managing diseased ocular tissue in the bulbar conjunctiva, comprises a contact lens substrate which comprises a substantially elliptical corneal portion and a limbus portion located radially about the corneal portion. In this device, a scleral portion is also located radially about the substrate. The device can be at least partially degradable and comprising a therapeutic compound. Moreover, at least a portion of the scleral portion can be configured to overlay, and deliver the therapeutic compound to, a diseased ocular tissue located adjacent to the cornea of a patient.

In yet another exemplary embodiment, a device comprises a contact lens substrate comprising a substantially elliptical corneal portion and a limbus portion located radially about the corneal portion. A scleral portion is located radially about the substrate. Moreover, the scleral portion extends nasally and temporally to overlay nasally and temporal bulbar conjunctiva and sclera to protect against ultraviolet damage and irritants.

BRIEF DESCRIPTION OF THE DRAWINGS

FIG. 1A is a perspective view of a microneedling device in accordance with an exemplary embodiment.

FIG. 1B is another perspective view of a microneedling device in accordance with an exemplary embodiment.

FIG. 1C is yet another perspective view of a microneedling device in accordance with an exemplary embodiment.

FIG. 1D is a perspective view illustrating attributes of a microneedling device in accordance with an exemplary embodiment.

FIG. 1E is a perspective view of a portion of a microneedling device in accordance with an exemplary embodiment.

FIG. 1F is a perspective view of a portion of a microneedling device in accordance with an exemplary embodiment.

DETAILED DESCRIPTION OF THE EMBODIMENTS

Figure 2A:
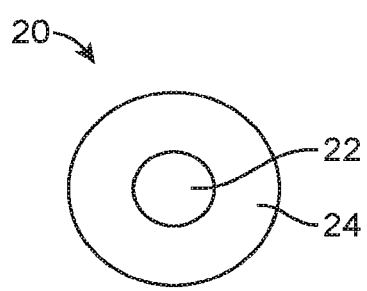
FIG. 2A is a top view of a circular contact lens device in accordance with an exemplary embodiment.

Methods and devices of the exemplary embodiments provide for treatment and management of a variety of ocular diseases and specifically target diseased ocular tissue. Moreover, the methods and devices can serve preventative, therapeutic and/or cosmetic purposes. As used herein "ocular disease" includes diseases, disorders, degenerative conditions, or any other abnormal ocular conditions. Furthermore, "diseased tissue" or "diseased ocular tissue" denote unhealthy or abnormal tissue. Examples include, but are not limited to, misaligned, tangled, cross-linked or otherwise abnormally structured fibrils. Finally, while some exemplary embodiments are presented in the context of pinguecula and pterygium, various other ocular diseases treatable or manageable in accordance with the embodiments are contemplated.

In exemplary embodiments, microneedling devices are provided for treating an ocular disease. Generally, the microneedling device comprises a plurality of microneedles arranged on a substrate. The microneedles may be in any arrangement and shape conducive to initiating collagen induction therapy as described in this disclosure. As further described in the present disclosure, the combination of the arrangement and shape of both substrate and microneedles may facilitate controlled conjunctival microinjury to trigger neocollagenesis and neoelastinogenesis within the bulbar conjunctiva.

FIGS. 1A-F illustrate a few examples of microneedling devices in accordance with exemplary embodiments. In FIG. 1A, the device 11 comprises a substrate 12 and a plurality of microneedles 13 arranged thereon. The substrate 12 shown is a rectangular in configuration. It is to be understood, of course, that the configuration and size of the substrate 12 may vary considerably depending on the particular use for which it is intended. Hence the substrate 12 may assume other configurations, such as circular, oval and triangular. Moreover, some or all corners and sides may be rounded. The substrate 12 shown comprises an upper surface 14 and lower surface 15. Moreover, the substrate 12 may be solid, hollow, or porous.

Essentially any biocompatible material may be suited for the substrate 12. Examples include, but are not limited to metals (ex. pharmaceutical grade stainless steel, gold, copper) or polymers (biodegradable or non-biodegradable). Examples of biodegradable polymers include collagen, hyaluronic acid, ascorbate, methylcellulose (and other cellulose esters), chitosan, polylactides, polyglycolides, poly-lactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Examples of non-biodegradable polymers include polyacrylates, polymers of ethylene-vinyl acetates and other acyl substituted cellulose acetates, non-degradable polyurethanes, polystyrenes, polyvinyl alcohol, polysurface capillary fiber, polyhydroxy ethyl methacrylate, polyvinyl chloride, polyvinyl fluoride, poly (vinyl imidazole), chlorosulphonate polyolefins, polyethylene oxide, blends and copolymers thereof. The substrate 12 may also comprise glycosaminoglycans (GAGs) such as hyaluronate, chondroitin sulfate, heparan sulfate, heparin, dermatan sulfate, keratin sulfate. Alternatively, the substrate 12 may be a composite comprising two or more of the materials provided. Moreover, substrate 12 may be entirely or partly coated with a therapeutic compound which is delivered to the diseased tissue during application.

The substrate 12 shown bestows a smooth surface to the ocular microneedling device and should be comfortable for the patient once applied against/to ocular tissue. Essentially, the substrate can take on any shape that allows for safe application of the device to a patent's eye. In particular, the shape of the substrate 12 may be planar, curved or a combination thereof. For instance, the substrate 12 may be unicurved to fit one radius of curvature, dual curved to fit two radii of curvature or multicurved to fit multiple radii of curvature based on the ocular tissue being treated. In an exemplary embodiment, the substrate comprises sufficient flexibility to at least partially conform to the shape of a raised tissue, such as a pinguecula. FIGS. 1B and 1C illustrate substrates bent in concave and convex shapes, although other modes of flexure are contemplated herein.

Advantageously, the devices of the exemplary embodiments may be designed to achieve maximum contact with the diseased tissue while avoiding certain sensitive portions of the eye. In such instances, the shape of the substrate may vary where all or a portion of the substrate may comprise microneedles. FIGS. 1E and 1D illustrate examples where certain substrate portions 19 lack microneedles. In particular, the example provided in FIG. 1D, the device 11 comprises a substantially circular substrate 12 with an opening 18 therein. The opening 18 may be dimensioned to receive the cornea without contacting the same. As such, the microneedles 12, may contact the Pinguecula near the cornea without contacting the cornea itself. Of course the substrate shape or microneedle coverage may accommodate for other sensitive areas besides the cornea.

The microneedling devices may be mechanically contacted with the diseased tissue. In exemplary embodiments, the substrate is connected to a drive unit or a handle. FIG. 1F provides an example where the substrate 12 is connected to a connector element 10. The connector element 10 may be connected to a drive unit (not shown) configured to position the device relative to the diseased tissue. The drive unit may comprise a feedback loop for continuously monitoring and adjusting the position of the device. Of course, the device position may be manually controlled.

The shape, configuration and arrangement of the microneedles may vary considerably depending on the desired application. In the example provided in FIG. 1A, solid, hollow, or porous microneedle(s) 13 stem off of the upper surface 14 of substrate 12. Substrate 12 serves to provide a stable supporting structure/base for the microneedles 13 to rest on. As illustrated, microneedle 13 has a conical configuration. However, the microneedle 13 may assume other configurations such as, but not limited to, pyramidal or cylindrical. Essentially, any geometry that can produce the micro-injury sites described is contemplated herein.

Additionally, all or some of the microneedles 13 may be arranged at an angle (less than or greater than 90 degrees) with respect to the upper surface 14 of the substrate 12. The tip 16 of the microneedle 13 may be many different configurations such as beveled, tapered, squared-off or rounded. However, a blunt or beveled tip would likely allow more ease of microneedle insertion into the ocular tissue. The base 17 of the microneedles 13 may have different size or shape diameters, and the microneedle length can vary between different regions of the substrate surface 14. Thus, microneedles with a variety of aspect ratios on the same device are possible. In addition, the spacing between microneedles 13 on the substrate 12 may vary across the substrate, if for example, more density is required.

The material of the microneedles 13 may be selected from various different biocompatible materials such as metals (e.g. pharmaceutical grade stainless steel, gold, copper) or polymers (e.g. biodegradable or non-biodegradable). Examples of biodegradable polymers include collagen, hyaluronic acid, ascorbate, methycellulose (including other cellulose esters), chitosan, polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Examples of non-biodegradable polymers include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), polyvinyl alcohol, polysurface capillary fiber, polyhydroxy ethyl methacrylate, chlorosulphonate polyolefins, polyethylene oxide, blends and copolymers thereof. Alternatively, the microneedles 13 may be a composite comprising two or more of any of these types of materials.

The microneedle 13 may be entirely or partly coated with one or more therapeutic compounds or contain within it one or more therapeutic compounds, such as ethylenediaminetetraacetic acid (EDTA), steroids, non-steroidal anti-inflammatory compounds, dipyridamole and platelet-rich plasma (PRP). Therapeutic compounds providing or causing the production of growth factors are specifically contemplated herein. The microneedle(s) 13 may also comprise glycosaminoglycans (GAGs) such as hyaluronate, chondroitin sulfate, heparan sulfate, heparin, dermatan sulfate or keratin sulfate.

In an exemplary embodiment, microneedling device 11 is dimensioned to enter the bulbar conjunctival stroma at an appropriate length to achieve controlled injury to the fibrous layer of the conjunctival stroma where there are collagen and elastin fibers. This controlled micro-injury site formation can cause collagen induction as disclosed herein. As a non-limiting example, the microneedle length is between about, 10 and 350 microns, preferably between 35 and 270 microns. In some cases the length is between about 250 and 300 microns. All integer values in these ranges are specifically contemplated.

In a general sense, the micro-injury sites formed in accordance with the exemplary embodiments may be regarded as a disruption in the fibrous ocular tissue layer. Thus in the exemplary embodiments the micro-injuries formed in the stroma may comprise, micro-pores, disrupted fibers, localized rupture of the vasculature, or combination thereof. In particular, localized rupture(s) of the vasculature can result in bleeding and release of growth factors which promote growth of new collagen and elastin fibrils. Additionally, the micro-pores can act as a receptacle for receiving therapeutic compounds including growth factors, anti-inflammatories and collagen as well as many other compounds as described herein.

Figure 7A:
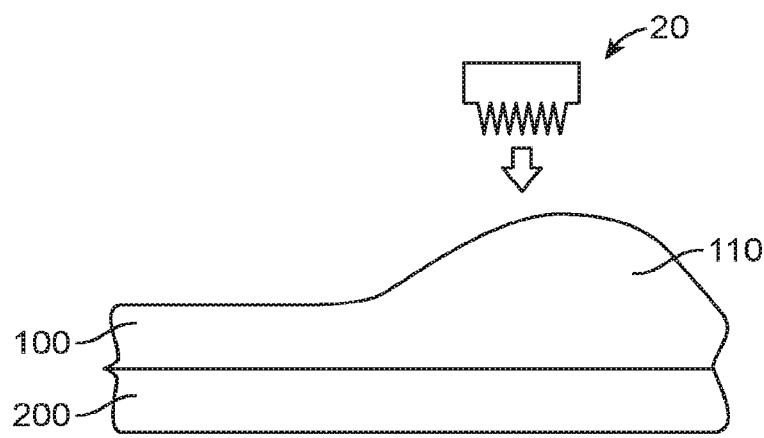
FIG. 7A is a schematic view conceptually illustrating the interaction between a microneedling device and ocular tissue.
Figure 7B:
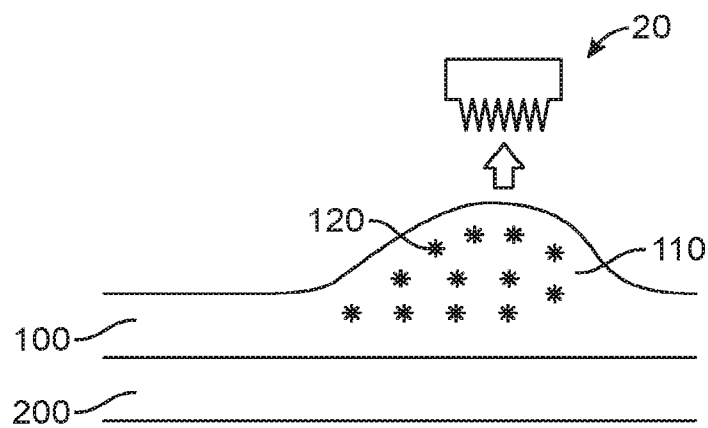
FIG. 7B is another schematic view conceptually illustrating the interaction between a microneedling device and ocular tissue.
Figure 7C:
FIG. 7C is a schematic view conceptually illustrating ocular tissue after interaction with a microneedling device.

A conceptual representation of the process of forming micro-injury sites within the diseased tissue is provided in FIGS. 7A-C. The relative sizes of the microneedles, the device 20 and the diseased tissue 110 can widely differ. Initially, per FIG. 7A, the microneedling device 20 is brought into contact with the diseased tissue region 110 of the conjunctiva 100. Although this tissue is shown in cross-section as a single raised feature, the shape could contain multiple bumps, plateaus with sharper peaks or broader peaks. The arrangement and shape of the microneedles may then vary based on the shape of the tissue 110, as further discussed below. Following contact with the diseased tissue 110 and retraction of the device 20, a plurality of micro-injury sites 120 remain in the diseased tissue 110, as shown in FIG. 7B. It should be noted that, although not shown, the device 20 may contact the healthy portion of the conjunctiva 100 or the scleral layer 200, to form micro-injuries therein as well.

In a sense, microneedling can create inflammation, proliferation and remodeling of the diseased tissue. Specifically, it is believed that the micro-injury sites activate matrix metalloproteinases (MMPs) which assist in several phases of wound healing. For instance in the inflammation of the tissue, the MMPs remove damaged extracellular matrix and bacteria. During the proliferation phase, the MMPs play a role in degradation of capillary basement membrane for angiogenesis as well as migration of epidermal cells. Further, the MMPs assist in remodeling the healing tissue.

Therefore, after forming the micro-injury sites 120, the unhealthy tissue is broken down, removed, whereby the growth factors help form new tissue 130 in place of the previous diseased tissue 120, as shown in 7C. Also the device may comprise therapeutic compounds that additionally provide or enhance the efficacy of the growth factors.

The following methods of manufacturing and application of a microneedling device are provided for exemplary purposes and are not intended to limit the scope of the exemplary embodiments. Other methods and variations are therefore contemplated herein. A uni-, bi- or multi-cavity casting mold can be used to produce a device with the desired overall dimensions with particular microneedle shapes and sizes. Initially, a casting solution containing the materials for the microneedles is placed in the microneedle cavity array, followed by drying or cross-linking the material. Next the solution containing the substrate material is in the substrate cavity and also dried or cross-linked. The substrate microneedles or both may have different zones of cross-linking which can be achieved by exposure to ultraviolet radiation. Crosslinking of all or parts of the ocular microneedling device could provide resistance to dissolution once applied to the ocular tissue, given that the greater degree of cross-linkage provides added resistance to enzymatic degradation. The device may be sterilized using chemical treatment, irradiation or other techniques known in the art. For instance, the device may be irradiated with gamma rays prior to packaging or use.

To begin application, a patient is prepared by applying an anesthetizing agent (ex. proparacaine eyedrop) to the eye, more specifically topically to the insertion site. The anesthetizing agent will reduce or eliminate pain that is caused by the application of the ocular microneedling device to the pinguecula. The ocular microneedling devices described herein, when contacted with conjunctival stroma, would likely cause an insignificant amount of pain when compared to conventional hypodermic needle penetration within ocular tissue.

After preparing the patient, a dehydrated ocular microneedling device is removed from within a sterile packet with the use of a medical forceps. A slit-lamp examination will be used to examine the ocular microneedle insertion site carefully. The eye care professional may determine the appropriate shape and features of the microneedling device in advance or at the time of application. The patient will be asked to look to his/her right to apply a microneedling device to a right eye nasal pinguecula. Alternatively, when applying to a right eye temporal pinguecula, patient will be asked to look to his/her left. Behind a biomicroscope, an eye care professional will safely use a medical forceps to apply the microneedle surface having sharp tips within the pinguecula. Therapeutic compounds may be applied to the microneedles if the device does not already contain such compounds. For instance before applying the device to a Pinguecula, the device may be dipped into a solution containing therapeutic compounds such as steroids, non-steroidal anti-inflammatory agents, dipyridamoles, platelet-rich plasma, or growth factors.

As described previously, the micro-injury sites formed using the microneedling device can comprise micron-size pores within the conjunctival stroma. In some instances it may be unlikely for certain therapeutic compounds (molecules) to normally diffuse into the epithelial barrier due to size or solubility. Therefore, advantageously, the micron-size pores may also serve as a direct pathway for drug molecule/particle introduction into ocular tissue. Microneedles made from or comprising therapeutic compounds may be degradable to locally deliver such compounds that assist with wound healing and collagen production. Moreover, the lateral/parallel orientation of collagen fibers of the conjunctival stroma will also assist with lateral diffusion of the therapeutic agents within the conjunctival stroma. Compounds such as collagen, hyularonic acid, and ascorbate may be used to reduce inflammation and assist wound healing by supporting collagen production within conjunctival stroma. Chitosan and methylcellulose may contribute to lubrication of the eye and minimizing dry eye symptoms. Steroid or non-steroidal anti-inflammatory agent may assist with reducing inflammation of the lesion. In addition, platelet-rich plasma will further support collagen production via release of growth factors.

In one embodiment, application of the microneedling device to the diseased tissue may further comprise electrical stimulation. For instance, an electric potential may be applied to conductive microneedles. It is believed that contacting the diseased tissue with microneedles and applying an electric potential thereto could promote release of various proteins, as well as potassium and growth factors from the cell to the exterior. As such, fibroblasts may migrate to the micro-injury site and promote collagen induction.

Diseased ocular tissue in the bulbar conjunctiva may be treated and managed using a device comprising contact lens substrate, as provided in this disclosure. In the exemplary embodiments, the device comprises a substrate portion and a scleral portion. In particular, the substrate comprises a substantially elliptical corneal portion. Essentially any elliptical shape suitable for enabling the device functionality is contemplated herein. As such, the elliptical shape may be shortened or elongated about either major or minor axis. In an exemplary embodiment, the corneal portion is substantially circular.

A limbus portion may be located radially about the corneal portion. The thickness of the radial portion may vary based on the desired coverage of the substrate, stability of the substrate, among other factors apparent from the instant disclosure. Moreover, the limbus portion may comprise the same material as the substrate or scleral portion, or a different material from these portions.

The scleral portion is located radially about the substrate portion and may comprise a therapeutic compound. Moreover, the scleral portion may be partially or entirely degradable as described further below. In the exemplary embodiments, the scleral portion may overlay one or more diseased tissue regions (treated or untreated) to protect the same from ultraviolet radiation, debris or any other type of irritant. Moreover, the scleral portion may deliver therapeutic compounds to the diseased tissue. Of course, the entire device as well may be deemed to protect the covered portions of a patient's eye from the aforementioned ultraviolet and other irritants.

Figure 2B:
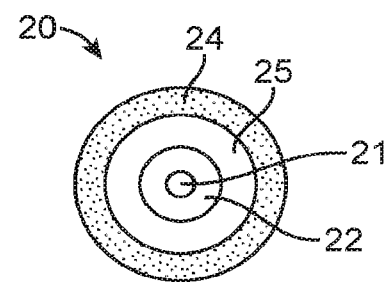
FIG. 2B is a top view of a circular contact lens device in accordance with an exemplary embodiment.

In the exemplary embodiment shown in FIG. 2A, the device 20 comprises a contact lens substrate comprising a radial portion 24 located radially about a central corneal portion 22. In particular, as shown in FIG. 2B, the device may comprise a pupil portion 21, located centrally within the corneal portion 22. Also, as shown corneal portion 22 is bounded by the limbus portion 25. Thus here, the limbus portion 25 is located between the corneal 22 and the scleral 24 portions. The thickness of the limbus portion 25 may be significantly smaller than that shown relative to the other portions. Moreover, when placed over the patient's eye, the limbus portion may overlap the patient's limbus, cornea, sclera or any combination thereof.

In exemplary embodiments, parts of or the entire scleral portion 24 may comprise microneedles as described previously. Here, the placement of the microneedles and the dimensions of the scleral portion preferably allow for maximum coverage of the diseased tissue. As such, the placement of the contact lens substrate on a patient's eye, would contact the diseased tissue such as a pinguecula or pterygium with the microneedles to potentially initiate collagen induction therapy.

Figure 2C:
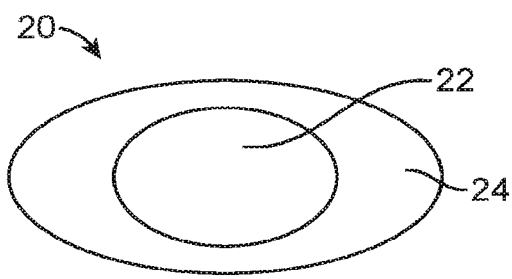
FIG. 2C is a top view of an oval contact lens device in accordance with an exemplary embodiment.

The device can take on any elliptical shape suitable for practicing the exemplary embodiments. For instance the substrate, scleral portion, or both may be circular. In the example shown in FIG. 2C, the shape of the device is an elongated ellipse. Specifically here both the substrate and the scleral portion 24 are elongated ellipses. Moreover, the relative size difference between the corneal and scleral portions can be larger or smaller than that shown. Also, the corneal portion may be circular while the scleral portion is an elongated ellipse.

All or portions of the device may be degradable. For example, the substrate may be formed from non-crosslinked degradable polymers, capable of rapid decomposition in the presence of enzymes in the tears, while the outer scleral portion may be formed from crosslinked degradable polymers, capable of a more slow decomposition in the presence of enzymes in the tears. Therefore, in such an example, after placement of the device on the eye, the substrate portion dissolves leaving, for example, the scleral portion. The resulting structure may be ring or a washer shaped around the eye's limbus, leaving the limbal portion, corneal portion and pupil portion of the eye uncovered. The remaining scleral portion, may or may not eventually dissolve.

In exemplary embodiments, the substrate and the scleral portion may comprise different materials. The substrate may include any material suitable for disease prevention, disease treatment, correction of visual acuity, cosmetics, or a combination thereof. In an exemplary embodiment, the substrate comprises a material suitable for contact lenses. In particular, this material could be suitable for hard, soft or hybrid contact lenses. A non-limiting example includes silicone hydrogel material. The scleral portion may include any therapeutic compound as explained below. A non-limiting example includes collagen. Advantageously, the combination of a silicone hydrogel contact lens substrate and a collagen scleral portion allows a user to obtain the lubrication and therapeutic benefits of the collagen upon degradation of the scleral portion, while retaining the visually corrective properties of the contact lens substrate.

Examples of therapeutic compounds include, but are not limited to, collagen, growth factors, steroids and anti-inflammatories. In particular, autologous platelet rich plasma (PRP) may be used which comprises a natural protein extracellular matrix that entraps various growth factors which stimulate cell proliferation, tissue healing and/or regeneration. Growth factors can include platelet-derived growth factors (PDGF), transforming growth factor-beta 1 (TGF-beta 1) and vascular endothelial growth factor (VEGF). Growth factors can be released by activating the platelets. In particular, PDGF can stimulate mitogenesis (cell replication/proliferation) and promote protein and collagen synthesis in wound healing. PDGF also induces the expression of TGF-beta 1. TGF-beta 1 initiates and terminates wound healing, as well as promotes cell differentiation and proliferation. TGF-beta 1 can also activate fibroblasts which proliferate to produce collagen.

The shape of the device may comprise one or more radii of curvature. Preferably, the portions of the device accommodate for different features of the eye as well as diseased tissue regions. For example, the substrate may be dual curved where the corneal portion's 22 curvature matches the curvature of the cornea, and likewise the curvature of the scleral portion 24 matches the scleral curvature. Advantageously, dual-curved or multi-curved scleral portions 24 can accommodate for different radius of curvature of a lesion (e.g. from pinguecula) on the bulbar conjunctiva. Also, the lesion may itself contain dual or multi radii of curvature that may be designed for. Further advantageously, the device curvature may accommodate for two different lesions on the nasal and/or temporal bulbar conjunctiva.

Figure 2D:
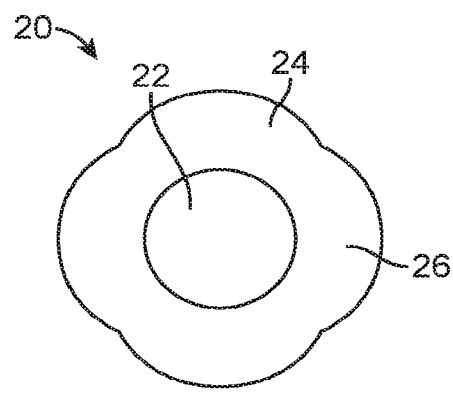
FIG. 2D is a top view of a contact lens device with extensions in accordance with an exemplary embodiment.

The device may further comprise extended scleral portions for further overlaying diseased tissue as well as delivering therapeutic compounds to different regions of the eye. In exemplary embodiments, the device may have one or more lateral or vertical extension portions of the scleral portion. For instance, FIG. 2D illustrates a device with lateral extensions 26 as well as vertical extensions. Preferably, the lateral extension portions extend over the sclera of the patient to overlay a diseased tissue such as a pinguecula. In some instance, such as the example of FIG. 2C, the elongated oval shape of the device may essentially provide the same coverage of a lateral scleral extension portion. Therefore, the composition, structure, and mechanical properties of the extension can be different from the rest of the device. The vertical scleral portions may provide an additional reach under the eyelids, for instance to locally deliver a therapeutic compound.

Figure 3A:
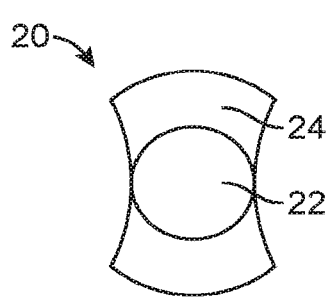
FIG. 3A is a top view of a circular contact lens device in accordance with an exemplary embodiment.
Figure 3B:
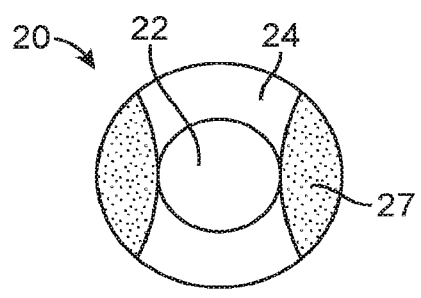
FIG. 3B is a top view of a circular contact lens device with degradable portions in accordance with an exemplary embodiment.
Figure 3C:
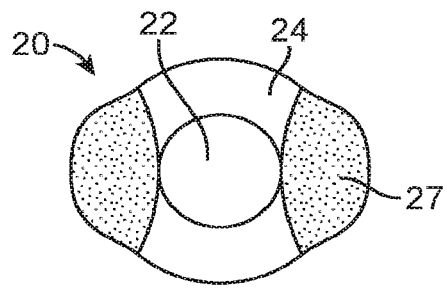
FIG. 3C is a top view of another contact lens device with extensions in accordance with an exemplary embodiment.

Scleral portions and extension portions may be partially or entirely degradable. Advantageously, the degradable portion can comprise a therapeutic compound that is directly delivered to the diseased tissue. Further advantageously, the remaining portion of the device (after partial dissolution) accommodates for the lesion, such that the device does not mechanically rub and irritate the lesion. This is illustrated in 3A-C and 4A-B. As shown, the device 20 in FIG. 3B comprises a substrate comprising a corneal portion 22 and a scleral portion 24. The degradable scleral portion 27 shown may overlap the diseased tissue and upon degradation, deliver therapeutic compounds to said tissue. FIG. 3C, provides a similar device where the degradable scleral portion 27 comprises an extended lateral portion. After dissolution of the degradable scleral portion 27, the rest of the device 20 remains, as shown in FIG. 3A. Advantageously, the resulting curved hourglass shape lacks temporal and/or nasal portions which avoid edge discomfort for contact lens patients with Pinguecula(e). Of course, the shape of the device, after dissolution of the certain portions, need not be hourglass shaped, and can take on other shapes to assist in minimizing edge discomfort.

Figure 4A:
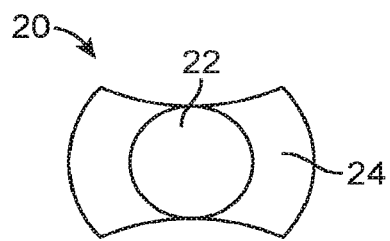
FIG. 4A is a top view of a contact lens device in accordance with an exemplary embodiment.
Figure 4B:
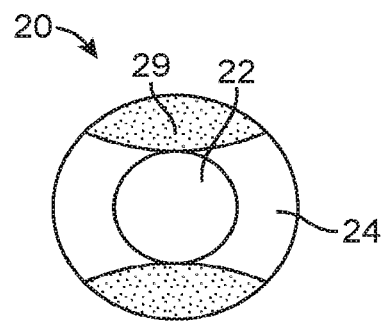
FIG. 4B is a top view of a contact lens device with degradable portions in accordance with an exemplary embodiment.

In some instances, it is beneficial to deliver a therapeutic compound to the tissue of the inner portion of the eyelid. To that end, the device may comprise vertical scleral portions that are degradable. Of course, it may be possible to contain both lateral and vertical degradable portions on the same device. Furthermore, the entire scleral portion may be degradable. As in the previous examples, the degradable scleral portion may take on different shapes, and could further comprise an extension portion. An example is provided in FIGS. 4A-B, where after the vertical scleral portion 29 of the device 20 dissolves, the resulting device resembles a horizontal hourglass.

Figure 6A:
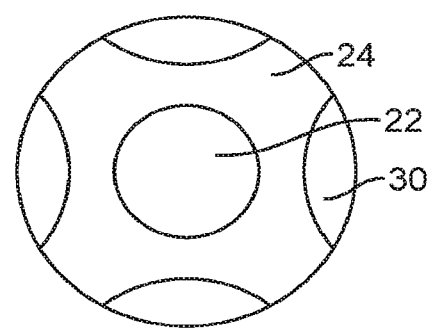
FIG. 6A is a top view of a contact lens device with degradable layers in accordance with an exemplary embodiment.
Figure 6B:
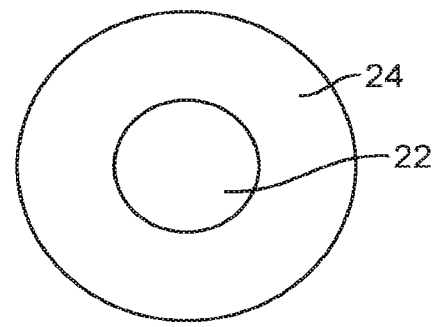
FIG. 6B is a top view of a contact lens device in accordance with an exemplary embodiment.

In an exemplary embodiment, the device comprises at least one degradable layer for delivering therapeutic compounds to the eye. For instance, in FIG. 6A, the device comprises a corneal portion 22, bounded by a scleral portion 24. On the scleral portion there are several therapeutic compound layers 30. Here, after dissolution which is shown in FIG. 6B, the structure and overall shape of the device remain unchanged. In some instances, it may be desirable to provide one continuous layer 30 covering the entire, scleral portion, and substrate portions. Moreover, in some instances, the therapeutic compound layer may be on the top side, underside, or both, of the device.

Figure 5:
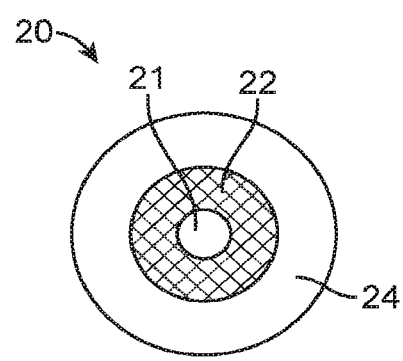
FIG. 5 is a top view of a contact lens device in accordance with another exemplary embodiment.

The exemplary embodiment illustrated in FIG. 5, provides an example where the corneal portion 22 of the substrate is colored for cosmetic purposes. Here, the device comprises a pupil portion 21 that is a central opening within the corneal portion 22. Similar to other embodiments the sclera portion 24 may further comprise degradable and non-degradable portions (not shown) as well as lateral and vertical extension portions (also not shown). Here, the benefits of treating and managing ocular disease, in a manner similar to above, may be achieved while providing additional cosmetic features of a colored lens substrate. Moreover, a patient without the need of corrective lens may derive the benefit of the entire device being formed from a degradable material comprising a therapeutic compound.

The detailed description and drawings presented in this disclosure are intended as a description of presently-preferred embodiments and are not intended to represent the only forms of the exemplary embodiments. Those of ordinary skill will understand and appreciate the existence of variations, combinations, and equivalents of the exemplary embodiments.

What is claimed is:

1. A device for treating and managing diseased ocular tissue in a patient's bulbar conjunctiva, comprising:
 a contact lens substrate configured to be placed on the patient's eye, comprising:
  a substantially elliptical corneal portion comprising a first material; and
  a continuous annular scleral portion comprising a second material and disposed radially about the corneal portion;
  wherein the scleral portion is configured to at least partially degrade, thereby delivering a therapeutic compound to a diseased ocular tissue adjacent to the patient's cornea, and
  wherein the first material is different from, and degrades at a slower rate than, the second material.

2. The device of claim 1, comprising a plurality of microneedles positioned on the scleral portion of the device, wherein the microneedles are arranged and dimensioned such that when the device is brought into contact with the diseased tissue, the microneedles penetrate a diseased ocular tissue region formed in the bulbar conjunctival stroma, to produce a plurality of micro-injury sites within the diseased bulbar conjunctival stroma region, and cause release of growth factors and formation of new collagen fibrils.

3. The device of claim 1, wherein the first material comprises a hydrogel.

4. The device of claim 1, wherein the device has a top side opposite an underside, and at least one degradable layer of a therapeutic compound on the top side or underside of the device.

5. The device of claim 1, wherein the substrate comprises an open central pupil portion centrally located within the corneal portion, and the corneal portion comprises a colored hydrogel.

6. A device for treating and managing diseased ocular tissue in a patient's bulbar conjunctiva, comprising:
 a contact lens substrate comprising:
  a non-degraded configuration comprising:
   a substantially elliptical corneal portion; and
   a continuous annular scleral portion disposed radially about the corneal portion, said scleral portion having at least one distinct degradable portion disposed adjacent to the corneal portion; and
  a degraded configuration comprising:
   a substantially elliptical corneal portion; and
   a non-continuous annular scleral portion disposed radially about the corneal portion, said scleral portion having a discontinuity corresponding to said at least one distinct degradable scleral portion;
 wherein the corneal portion comprises a first material and the degradable scleral portion comprises a second material, said first and second materials being different from each other, and
 wherein the contact lens substrate is configured to transition from the non-degraded configuration to the degraded configuration after contacting the patient's eye.

7. The device of claim 6, wherein in the degraded configuration the contact lens substrate comprises a concave portion defining a discontinuity in the scleral portion.

8. The device of claim 7, wherein in the non-degraded configuration the scleral portion comprises two distinct degradable portions disposed on opposing sides of the corneal portion.

9. The device of claim 8 wherein in the degraded configuration the substrate comprises two distinct scleral portions disposed on opposing sides of the corneal portion.

10. The device of claim 6, wherein in the degraded configuration the substrate is hourglass shaped.

11. The device of claim 6, wherein in the non-degraded configuration, the scleral portion comprises a plurality of microneedles.

12. The device of claim 6, wherein the first material comprises a hydrogel material.

13. The device of claim 12, wherein the first material comprises a silicon hydrogel.

14. The device of claim 6, wherein the second material comprises a biocompatible material.

15. The device of claim 1, wherein the second material is less crosslinked than the first material.

16. The device of claim 1, wherein the first material comprises a hydrogel.

17. The device of claim 16, wherein the first material is a visually corrective silicon hydrogel material.

18. The device of claim 16, wherein the second material comprises a biocompatible material.

19. The device of claim 1, further comprising a continuous annular limbus portion disposed between the corneal portion and scleral portion, the limbus portion comprising a third material which is different from the first and second material.

20. The device of claim 2, wherein the plurality of microneedles rapidly decompose following contact with the patient's eye.

21. The device of claim 20, wherein the microneedles comprise the second material.

22. The device of claim 20, wherein the microneedles comprise a third material which is different from the first and second material.

23. The device of claim 1, wherein the scleral portion comprises at least one lateral extension which comprises a third material and degrades after contacting the patient's eye.

24. The device of claim 1, wherein the scleral portion comprises at least one lateral extension which comprises a different radius of curvature than the corneal portion.

* * * * *